(12) United States Patent
Linderman

(10) Patent No.: US 6,720,450 B2
(45) Date of Patent: Apr. 13, 2004

(54) PESTICIDAL ACTIVITY OF FUNCTIONALIZED CYCLOPROPANES

(75) Inventor: Russell J. Linderman, Green Oaks, IL (US)

(73) Assignee: North Carolina State University, Raleigh, NC (US)

( * ) Notice: Subject to any disclaimer, the term of this patent is extended or adjusted under 35 U.S.C. 154(b) by 55 days.

(21) Appl. No.: 10/020,835

(22) Filed: Dec. 13, 2001

(65) Prior Publication Data

US 2003/0149103 A1 Aug. 7, 2003

(51) Int. Cl.⁷ .............................................. C07C 51/36
(52) U.S. Cl. ....................................... 562/592
(58) Field of Search ......................... 562/592

(56) References Cited

U.S. PATENT DOCUMENTS

| | | |
|---|---|---|
| 4,204,071 A | 5/1980 | Anderson et al. |
| 4,897,397 A | 1/1990 | Shih et al. |
| 4,933,367 A | 6/1990 | Wolff et al. |
| 5,011,909 A | 4/1991 | Borovsky et al. |
| 5,130,253 A | 7/1992 | Borovsky et al. |
| 5,358,934 A | 10/1994 | Borovsky et al. |
| 5,555,366 A | 9/1996 | Teig et al. |
| 5,747,537 A | 5/1998 | Gordon et al. |
| 6,413,530 B1 | 7/2002 | Borovsky et al. |

FOREIGN PATENT DOCUMENTS

| | | |
|---|---|---|
| EP | 0428276 A2 | 5/1991 |
| GB | 2005271 A | 4/1979 |
| WO | WO 00/18920 | 4/2000 |
| WO | WO 00/63233 | 10/2000 |
| WO | WO 00/63235 | 10/2000 |
| WO | WO 01/41543 | 6/2001 |

OTHER PUBLICATIONS

International Search Report for International Application Ser. No. PCT/US02/39755 dated Mar. 5, 2003.

Ansell et al., *Reduced Cyclic Compounds. Part XI. The Cyclisation of ωArylalkenoic Acids*, J. Chem. Soc., pp. 206–212 (1961).

Kishore, Nandini S., et al., *The Substrate Specificity of Saccharomyces cerevisiae Myristoyl–CoA: Protein N–Myristoyltransferase;*, The Journal of Biological Chemistry, vol. 266, No. 14, pp. 8835–8855 (May 15, 1991).

*Primary Examiner*—Alan L. Rotman
*Assistant Examiner*—Taylor V. Oh
(74) *Attorney, Agent, or Firm*—Myers Bigel Sibley & Sajovec

(57) ABSTRACT

The present invention provides functionalized cyclopropane compounds that have pesticidal and/or TMOF activity. The pesticidal compounds and other compounds of the present invention are usefully employed in the control of pests, particularly insect pests such as mosquitoes, which ingest blood.

86 Claims, No Drawings

PESTICIDAL ACTIVITY OF FUNCTIONALIZED CYCLOPROPANES

FIELD OF THE INVENTION

The present invention concerns functionalized cyclopropanes that have pesticidal activity, along with methods of use thereof.

BACKGROUND OF THE INVENTION

Many blood-ingesting pests are known to feed on humans and animals, and many pests are vectors for pathogenic microorganisms that threaten human and animal health, including commercially important livestock, pets and other animals. Various species of mosquitoes, for example, transmit diseases caused by viruses, and many are vectors for disease-causing nematodes and protozoa. Mosquitoes of the genus Anopheles transmit Plasmodium, the protozoan that causes malaria, a devastating disease which results in approximately 1 million deaths annually. The mosquito species *Aedes aegypti* transmits an arbovirus that causes yellow fever in humans. Other arboviruses transmitted by Aedes species include the causative agents of dengue fever, eastern and western encephalitis, Venezuelan equine encephalitis, St. Louis encephalitis, chikungunya, oroponehe and bunyarnidera. The genus Culex, which includes the common house mosquito *C. pipiens*, is implicated in the transmission of various forms of encephalitis and filarial worms. The common house mosquito also transmits *Wuchereria banuffi* and *Brugia malayi*, which cause various forms of lymphatic filariasis, including elephantiasis. *Trypanasomas cruzi*, the causative agent of Chagas' disease, is transmitted by various species of blood-ingesting Triatominae bugs. The tsetse fly (Glossina spp.) transmits African trypanosomal diseases of humans and cattle. Many other diseases are transmitted by various blood-ingesting pest species. The order Diptera contains a large number of blood-ingesting and disease-bearing insects, including, for example, mosquitoes, black flies, no-see-ums (punkies), horse flies, deer flies and tsetse flies.

Various pesticides have been employed in efforts to control or eradicate populations of disease-bearing pests, such as disease-bearing blood-ingesting pests. For example, DDT, a chlorinated hydrocarbon, has been used in attempts to eradicate malaria-bearing mosquitoes throughout the world. Other examples of chlorinated hydrocarbons are BHC, lindane, chlorobenzilate, methoxychlor, and the cyclodienes (e.g., aldrin, dieldrin, chlordane, heptachlor, and endrin). The long-term stability of many of these pesticides and their tendency to bioaccumulate render them particularly dangerous to many non-pest organisms.

Another common class of pesticides is the organophosphates, which is perhaps the largest and most versatile class of pesticides. Organophosphates include, for example, parathion, Malathion, diazinon, naled, methyl parathion, and dichlorvos. Organophosphates are generally much more toxic than the chlorinated hydrocarbons. Their pesticidal effect results from their ability to inhibit the enzyme cholinesterase, an essential enzyme in the functioning of the insect nervous system. However, they also have toxic effects on many animals, including humans.

The carbamates, another group of pesticides, include such compounds as carbamyl, methomyl, and carbofuran. These compounds are rapidly detoxified and eliminated from animal tissues. Their toxicity is thought to involve a mechanism similar to the mechanism of the organophosphates; consequently, they exhibit similar shortcomings, including animal toxicity.

A major problem in pest control results from the capability of many species to develop pesticide resistance. Resistance results from the selection of naturally-occurring mutants possessing biochemical, physiological or behavioristic factors that enable the pests to tolerate the pesticide Species of Anopheles mosquitoes, for example, have been known to develop resistance to DDT and dieldrin. DDT substitutes, such as Malathion™, propoxur and fenitrothion are available; however, the cost of these substitutes is much greater than the cost of DDT.

There is clearly a longstanding need in the art for pesticidal compounds that are pest-specific, that reduce or eliminate direct and/or indirect threats to human health posed by presently available pesticides, that are environmentally compatible in the sense that they are biodegradable, are not toxic to non-pest organisms, and have reduced or no tendency to bioaccummulate.

Many pests, including for example blood-imbibing pests, must consume and digest a proteinaceous meal to acquire sufficient essential amino acids for growth, development and the production of mature eggs. Adult pests, such as adult mosquitoes, need these essential amino acids for the production of vitellogenins by the fat body. These-vitellogenins are precursors to yolk proteins which are critical components of oogenesis. Many pests, such as house flies and mosquitoes, produce oostatic hormones that inhibit egg development by inhibiting digestion of the protein meal and thereby limiting the availability of the essential amino acids necessary for egg development.

Serine esterases such as trypsin and trypsin-like enzymes (collectively referred to herein as "TTLE") are important components of the digestion of proteins by insects. In the mosquito, *Aedes aegypti*, an early trypsin that is found in the midgut of newly emerged females is replaced, following the blood meal, by a late trypsin. A female mosquito typically weighs about 2 mg and produces 4 to 6 ug of trypsin within several hours after ingesting a blood meal. Continuous biosynthesis at this rate would exhaust the available metabolic energy of a female mosquito; as a result, the mosquito would be unable to produce mature eggs, or even to find an oviposition site. To conserve metabolic energy, the mosquito regulates TTLE biosynthesis with a peptide hormone named Trypsin Modulating Oostatic Factor (TMOF). Mosquitoes produce TMOF in the follicular epithelium of the ovary 12–35 hours after a blood meal; TMOF is then released into the hemolymph where it binds to a specific receptor on the midgut epithelial cells, signaling the termination of TTLE biosynthesis. This regulatory mechanism is not unique for mosquitoes; flesh flies, fleas, sand flies, house flies, dog flies and other insect pests which need protein as part of their diet have similar regulatory mechanisms.

In 1985, Borovsky purified an oostatic hormone 7,000-fold and disclosed that injection of a hormone preparation into the body cavity of blood imbibed mosquitoes caused inhibition of egg development and sterility (Borovsky, D. [1985] *Arch. Insect Biochem. Physiol.* 2:333–349). Following these observations, Borovsky (Borovsky, D. [1988] *Arch. Ins. Biochem. Physiol.* 7:187–210) reported that injection or passage of a peptide hormone preparation into mosquitoes inhibited the TTLE biosynthesis in the epithelial cells of the gut. This inhibition caused inefficient digestion of the blood meal and a reduction in the availability of essential amino acids translocated by the hemolymph, resulting in arrested egg development in the treated insect.

Borovsky observed that this inhibition of egg development does not occur when the oostatic hormone peptides are inside the lumen of the gut or other parts of the digestive system (Borovsky, D. [1988], supra).

Following the 1985 report, the isolated hormone, (a ten amino acid peptide) and two TMOF analogues were disclosed in U.S. Pat. Nos. 5,011,909 and 5,130,253, and in a 1990 publication (Borovsky et al. [1990] *FASEB J.* 4:3015–3020). Additionally, U.S. Pat. No. 5,358,934 discloses truncated forms of the full length TMOF which have prolines removed from the carboxy terminus, including the peptides YDPAP, YDPAPP, YDPAPPP, and YDPAPPPP.

D. Borovsky and R. Linderman, U.S. patent application Ser. No. 09/295,996, filed Apr. 21, 1999, discloses additional novel peptides and the use thereof to control insect pests.

TMOF analogs that have been identified to date are primarily peptide analogs. In order to provide a greater diversity of new pesticidal compounds, it would be desirable to possess compounds that are TMOF analogues, yet are not peptides.

SUMMARY OF THE INVENTION

The present invention is based, inter alia, on the discovery of non-peptide organic compounds that act like TMOF, signaling the termination of TTLE biosynthesis and have pesticidal activity. Thus the present invention concerns pesticidal compounds that inhibit digestion in pests by terminating or otherwise blocking synthesis of digestive enzymes by activating a TMOF receptor (collectively referred to herein as "pesticidal compounds"). The invention also comprehends structurally related compounds that have pesticidal and/or pest-repellant applicability. The pesticidal compounds and other compounds of the present invention are usefully employed in the control of pests, particularly insect pests such as mosquitoes, which ingest blood.

Thus, a first aspect of the present invention is a method of controlling a pest such as an insect pest, comprising administering to said pest a pesticidally effective amount of a non-peptide TMOF analog (that is, an organic compound that has TMOF activity). This definition is specifically intended to exclude the peptide TMOF agonists or analogs disclosed in, inter alia, U.S. Pat. Nos. 5,011,909; 5,130,253; and 5,358,934, the disclosures of which are incorporated by reference herein in their entirety.

Particular pesticidal compounds/non-peptide TMOF analogs of the present invention have the formula I below:

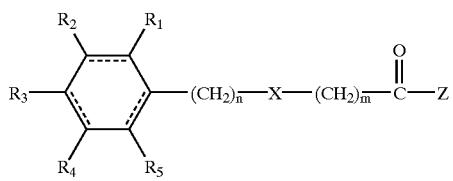
(I)

wherein:
X is a cyclopropyl group of the formula —CHCH$_2$CH—;
Z is selected from the group consisting of —OH, —NH$_2$, —NHR$_6$ and —OR$_6$
wherein R$_6$ is alkyl, alkenyl, optionally substituted cycloalkylalkyl, and optionally substituted aralkyl;
m≧0 and n≧1 and (m+n) can have any integer value from 1 to 12 inclusive;
the ring bearing substituents R$_1$, R$_2$, R$_3$, R$_4$ and R$_5$ is a phenyl ring or a cyclohexyl ring, or a corresponding ring wherein one or more ring carbon atom(s) has been replaced by nitrogen atom(s);
R$_1$, R$_2$, R$_3$, R$_4$, and R$_5$ are each independently selected from the group consisting of —H, —OH, halo, loweralkyl, loweralkoxy, nitro, amino, and phenyl; subject to the proviso that:
when the ring is a phenyl ring, a pair of R$_1$ and R$_2$, R$_2$ and R$_3$, or R$_3$ and R$_4$ on the phenyl ring may together represent —CR$_7$=CR$_8$—CR$_9$=CR$_{10}$—, to form with the phenyl ring illustrated above a naphthyl ring system, wherein R$_7$, R$_8$, R$_9$, and R$_{10}$ are each independently selected from the group consisting of —H, —OH, halo, nitro, amino, loweralkyl, and loweralkoxy.

The invention further contemplates acid, salt and ester forms of the foregoing compounds which have pest-controlling efficacy, as may be readily synthesized and demonstrated to be effective, within the skill of the art.

A second aspect of the present invention is a method of initiating a TMOF receptor-mediated biological response. The method comprises contacting to a TMOF receptor in vivo or in vitro for a time and in an amount sufficient to initiate a TMOF receptor-mediated biological response a compound of Formula I as described herein. The biological response may be any suitable biological response mediated by the TMOF receptor, including but not limited to inhibition of biosynthesis of a digestive enzyme such as trypsin.

The utility of the compounds and compositions of the invention is broadly contemplated as encompassing the mediation of pest-controlling biological responses in pest species, whether or not receptor-specific in character, and therefore other mechanisms that are pest-controlling in effect are within the purview of the invention.

As noted above, the pesticidal compounds of the present invention have advantageous biological activity against pests. The novel compounds of the invention are particularly active against blood-sucking insects, particularly against species of mosquitoes such as *Aedes aegypti* that are common vectors of arthropod-borne viral diseases, such as arboviruses. Other biting pests such as flies, fleas, ticks, and lice can also be controlled using compounds and methods of the subject invention. These pests utilize TTLE as their primary blood-digesting enzymes.

The subject compounds can also be used to control pests of agricultural crops, for example by applying the compounds to the agricultural crops. These pests include, for example, coleopterans (beetles), lepidopterans (caterpillars), and mites. The compounds of the subject invention can also be used to control household pests including, but not limited to, ants and cockroaches.

Another aspect of the subject invention pertains to a method for controlling pests, particularly insect pests, comprising administering to said pest a pesticidally effective amount of a pesticidal compound of the subject invention.

The subject invention provides pest control compositions comprising pesticidal compounds and a suitable pesticidal carrier. The pest control compositions are formulated for application to the target pests or their situs.

The methods and materials of the subject invention provide a novel approach to controlling insects and insect-transmitted diseases. The compounds of the subject invention have advantageous activity and increased resistance to proteolysis over previously disclosed compounds.

While the present invention is in part explained with reference to TMOF activity, it will be appreciated that this statement of underlying activity is provided for explanation, and that applicants do not intend to be bound by any particular theory of the invention. For example, the compounds of the invention may also be used as pest or insect repellants, and the compounds of the invention may control pests or insects by mechanisms in addition to, or different from, TMOF activity.

The present invention is explained in greater detail below.

DETAILED DESCRIPTION OF THE PREFERRED EMBODIMENTS

As used herein, the term "pesticidally effective" is used to indicate an amount or concentration of a pesticidal compound which is sufficient to reduce the number of pests in a geographical locus as compared to a corresponding geographical locus in the absence of the amount or concentration of the pesticidal compound.

The term "pesticidal" is not intended to refer only to the ability to kill pests, such as insect pests, but also includes the ability to interfere with a pest's life cycle in any way that results in an overall reduction in the pest population and/or mitigates negative impact of insects on targeted uses. For example, the term "pesticidal" includes inhibition of a pest from progressing from one form to a more mature form, e.g., transition between various larval instars or transition from larva to pupa or pupa to adult. Further, the term "pesticidal" is intended to encompass anti-pest activity during all phases of a pest's life cycle; thus, for example, the term includes larvacidal, ovicidal, pupacidal, and adulticidal activity.

The invention also contemplates uses of the compounds and compositions of the invention for anti-pest activity involving repellant action.

The term "loweralkyl" as used herein means $C_1$ to $C_6$ alkyl. Preferred loweralkyl species include $C_1$ to $C_4$ alkyl, and most preferably, loweralkyl is methyl, ethyl or propyl. Loweralkyl species can be of straight chain or branched conformations, as necessary or desired in a specific application of the invention. "Alkyl" per se includes alkyl substituents of any carbon number, e.g., in a range of $C_1$–$C_{30}$, which are efficacious to provide compounds of a pest-controlling character.

The term "loweralkoxy" as used herein means $C_1$ to $C_6$ alkoxy. Preferred loweralkoxy species include $C_1$ to $C_4$ alkoxy, and most preferably, loweralkoxy is methoxy, ethoxy, or propoxy. Loweralkoxy species can be of straight chain or branched conformations, as necessary or desired in a specific application of the invention.

The term "alkenyl" as used herein means $C_1$ to $C_{12}$ alkenyl. Preferred alkenyl species include $C_1$ to $C_8$ alkenyl, more preferably $C_1$ to $C_6$ alkenyl and most preferably $C_1$ to $C_4$ alkenyl.

The term "optionally substituted cycloalkylalkyl" as used herein means cycloalkylalkyl whose cycloalkyl moiety is $C_3$–$C_{12}$ cycloalkyl, more preferably $C_3$–$C_{10}$ cycloalkyl, and most preferably $C_3$–$C_6$ cycloalkyl, and whose remaining alkyl moiety is $C_1$–$C_{12}$ alkyl, more preferably $C_1$–$C_8$ alkyl, and most preferably $C_1$–$C_6$ alkyl, wherein the respective cycloalkyl and/or remaining alkyl moieties can be optionally substituted with compatible substituents such as loweralkyl, loweralkoxy, halo, hydroxy, amino, nitro, etc. which do not preclude the efficacy of the compound for its intended use.

The term "optionally substituted aralkyl" as used herein means aralkyl whose aryl moiety is $C_5$–$C_{12}$ aryl, and more preferably $C_5$–$C_{10}$ cycloalkyl, and whose alkyl moiety is $C_1$–$C_{12}$ alkyl, more preferably $C_1$–$C_8$ alkyl, and most preferably $C_1$–$C_6$ alkyl, wherein the respective aryl and/or alkyl moieties can be optionally substituted with compatible substituents such as loweralkyl, loweralkoxy, halo, hydroxy, amino, nitro, etc. which do not preclude the efficicacy of the compound for its intended use.

The term "halo" as used herein means halogen, preferably fluoro, chloro, bromo or iodo, most preferably fluoro.

1. Pesticidal Compounds.

Compounds useful in the present invention include those of the general formula I below, as well as corresponding salt, ester and acid forms thereof:

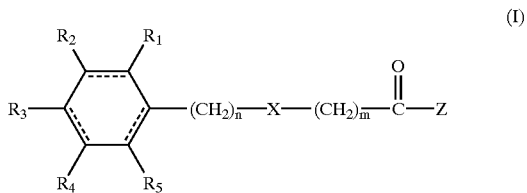

(I)

wherein:

X is a cyclopropyl group of the formula —CHCH$_2$CH—;

Z is selected from the group consisting of —OH, —NH$_2$, —NHR$_6$ and —OR$_6$ wherein R$_6$ is alkyl, alkenyl, optionally substituted cycloalkylalkyl, and optionally substituted aralkyl;

m≧0 and n≧1 and together total an integer from 1 to 12;

the ring bearing substituents R$_1$, R$_2$, R$_3$, R$_4$ and R$_5$ is a phenyl ring or a cyclohexyl ring, or a corresponding ring wherein one or more ring carbon atom(s) has been replaced by nitrogen atom(s); and R$_1$, R$_2$, R$_3$, R$_4$, and R$_5$ are each independently selected from the group consisting of —H, —OH, halo, loweralkyl, loweralkoxy, nitro, amino, and phenyl; subject to the proviso that:

when the ring is a phenyl ring, a pair of R$_1$ and R$_2$, R$_2$ and R$_3$, R$_3$ and R$_4$, or R$_4$ and R$_5$ on the phenyl ring may together represent —CR$_7$=CR$_8$—CR$_9$=CR$_{10}$—, to form with the phenyl ring illustrated above a naphthyl ring system, wherein R$_7$, R$_8$, R$_9$, and R$_{10}$ are each independently selected from the group consisting of —H, —OH, halo, nitro, amino, loweralkyl, and loweralkoxy.

In one preferred group of compounds of formula I above, n and m are each at least 1 and together total an integer from 2, 3 or 4 to 6, 8, 10 or 12.

The present invention contemplates variously preferred sub-genera of the Formula I non-peptide TMOF-analog pesticidal compounds, wherein (m+n) has a numerical range of integer values in which the lower numerical value of the range can be any integer from 1 to 12 and in which the upper numerical value of the range may each have any value in the range of 2 to 12, subject to the proviso that the upper numerical value is of course greater than the lower numerical value.

The invention also contemplates sub-genera of the Formula I non-peptide TMOF-analog pesticidal compounds, wherein (m+n) has any of various permutative combinations of single integer values selected from the range of from 1 to 12, e.g., the quantity (m+n) in one embodiment may equal 1, 2, 6 or 7, and in another embodiment the quantity (m+n) may equal 3, 4 or 9.

Sub-genera of the Formula I compounds include, for example, those in which each of the integer values n and m for the respective numbers of repeating methylene (—CH$_2$—) units flanking the cyclopropyl group is independently in a range of from 1 to 6, or alternatively from 1 to 4, from 2 to 4, or from 2 to 3.

In another preferred group of compounds of formula I above, the ring is a phenyl ring.

In another preferred group of compounds of formula I above, the ring is a cyclohexyl ring.

In another preferred group of compounds of formula I above, the ring corresponds to a phenyl ring or a cyclohexyl ring, wherein one or more ring carbon atom(s) has been replaced by nitrogen atom(s). For example, the ring may be pyridinyl, pyridazinyl, pyrimidinyl, pyrazinyl, piperidinyl, piperazinyl, triazinyl, etc.

In another preferred group of compounds of formula I above, m is 0.

In another preferred group of compounds of formula I above, at least one of $R_1$, $R_2$, $R_3$, $R_4$ or $R_5$ is phenyl (Ph)

Compounds of the present invention can be made by the techniques described in the Examples below, or variations thereof that will be apparent to those skilled in the art.

Compounds of the present invention can be made by the technique described in M. Ansell and J. Ducker, Reduced cyclic Compounds. Part XI. The Cyclisation of ω-Arylalkenoic Acids, *J. Chem. Soc.* 206–212 (1961), or variations thereof that will be apparent to those skilled in the art.

A further aspect of the subject invention relates to addition salts, complexes, or prodrugs such as esters of the compounds described herein, especially the nontoxic pharmaceutically or agriculturally acceptable acid addition salts. The acid addition salts can be prepared using standard procedures in a suitable solvent from the parent compound and an excess of an acid, such as hydrochloric, hydrobromic, sulfuric, phosphoric, acetic, maleic, succinic, ethanedisulfonic or methanesulfonic acids. Esterification to form derivatives such as the methyl or ethyl esters, can also be performed using standard procedures. Tartarate salts can be prepared in accordance with standard procedures.

Also, derivation of the pesticidal compounds with long chain hydrocarbons will facilitate passage through the cuticle into the pest body cavity. Therefore, in a further embodiment, the subject invention provides compositions comprising the pesticidal compounds bound to lipids or other carriers.

2. Methods and Formulations for Control of Pests.

The subject invention concerns novel pest control compounds and methods for using such compounds. Specifically exemplified are novel pesticidal compounds, compositions comprising said pesticidal compounds and the use of such pesticidal compounds and compositions in controlling pests, particularly insect pests such as mosquitoes.

Preferably, the subject compounds have an LD50 against mosquito larvae of less than 3.0 mM/L. More preferably, the compounds have an LD50 of less than 2.0 mM/L, and, most preferably, the compounds have an LD50 of less than 1.0 mM/L. As used herein, "LD50" refers to a lethal dose of a peptide pest-controlling compound of the invention that is able to cause 50% mortality of larvae maintained on a diet of 1 mg/ml autoclaved yeast supplemented with the pesticidal polypeptide. The term "$LC_{50}$" also is used hereinafter and refers to the concentration of a pest-controlling compound of the invention in the ambient environment of the pest species that is able to cause a 50% mortality of such species. For example, in tests described hereinafter, wherein compounds of the invention are tested for pesticidal efficacy against mosquito larvae, the compounds are present in a state of dynamic equilibrium in the aqueous environment containing the yeast and are taken up by the filter-feeding mosquito larvae during their feeding on the yeast. The $LC_{50}$ concentration values set out hereinafter are specified in milliMolar (mM) units, it being apparent that corresponding LD50 values (reflecting actual intake of the compound by the mosquito larvae) are substantially less than the $LC_{50}$ values, as a result of the dispersed and distributed character of the compounds in the aqueous medium containing the yeast.

Mosquito larval mortality was followed for three days in microtiter plates containing 160 μL sterile water, 1–4 μL of the test compound dissolved in dimethylsulfoxide, and 10 μL of 2% Brewer's yeast.

Control of pests using the pest control compounds of the subject invention can be accomplished by a variety of methods known to those skilled in the art. The plant pests that can be controlled by the compounds of the subject invention include pests belonging to the orders Coleoptera, Lepidopterans, Hemiptera and Thysanoptera. These pests all belong to the phylum Arthropod. Other pests that can be controlled according to the subject invention include members of the orders Diptera, Siphonaptera, Hymenoptera and Phthiraptera. Other pests that can be controlled by the compounds of the subject invention include those in the family Arachnida, such as ticks, mites and spiders.

The use of the compounds of the subject invention to control pests can be accomplished readily by those skilled in the art having the benefit of the instant disclosure. For example, the compounds may be encapsulated, incorporated in a granular form, solubilized in water or other appropriate solvent, powdered, and included into any appropriate formulation for direct application to the pest or to a pest inhabited locus.

Formulated bait granules containing an attractant and the pesticidal compounds of the present invention can be applied to a pest-inhabited locus, such as to the soil. Formulated product can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants.

Liquid formulations may be aqueous-based or non-aqueous (i.e., organic solvents), or combinations thereof, and may be employed as foams, gels, suspensions, emulsions, microemulsions or emulsifiable concentrates or the like. The ingredients may include rheological agents, surfactants, emulsifiers, dispersants or polymers.

As would be appreciated by a person skilled in the art, the pesticidal concentration will vary widely depending upon the nature of the particular formulation, particularly whether it is a concentrate or to be used directly. The pesticidal compound will be present in the composition by at least about 0.0001% by weight and may be 99 or 100% by weight of the total composition. The pesticidal carrier may be from 0.1% to 99.9999% by weight of the total composition. The dry formulations will have from about 0.0001–95% by weight of the pesticide while the liquid formulations will generally be from about 0.0001–60% by weight of the solids in the liquid phase. These formulations will be administered at about 50 mg (liquid or dry) to 1 kg or more per hectare.

The formulations can be applied to the pest or the environment of the pest, e.g., soil and foliage, by spraying, dusting, sprinkling or the like.

The pest control compounds may also be provided in tablets, pellets, briquettes, bricks, blocks and the like which are formulated to float, maintain a specified depth or sink as desired. In one embodiment the formulations, according to the present invention, are formulated to float on the surface of an aqueous medium; in another embodiment they are formulated to maintain a depth of 0 to 2 feet in an aqueous medium; in yet another embodiment the formulations are formulated to sink in an aqueous environment.

The term "control" is intended to include control by repelling insects, as discussed in greater detail below.

3. Repellant Methods and Compositions.

In insect repellant methods, the insect is administered the active agent by applying the active agent to a subject or substrate in an amount sufficient to repel insects.

Subjects to be treated with compounds of the present invention include both human and animal subjects (e.g., dogs, cats, horses, cattle). Subjects may be directly or indirectly treated, such as by applying the active compound to the skin of the subject, or by applying the active compound to an article worn by or otherwise protecting the subject.

Substrates to be treated with compounds of the present invention include, but are not limited to, floors, plants, containers, walls, pools or open bodies of water, etc.

Insects that may be repelled by the methods of the present invention include ticks, fleas, cockroaches, and biting flies, typically of the order Diptera, and further including mosquitoes, horse flies, deer flies, black flies, gnats, no-see ums, chiggers, etc.

The term "mosquito" as used herein concerns any type of mosquito (e.g., Anopheles, Aedes, and Culex), including but not limited to Tiger mosquitoes, *Aedes aboriginis, Aedes Aegypti, Aedes, albopictus, Aedes cantator, Aedes sierrensis, Aedes sollicitans, Aedes squamiger, Aedes sticticus, Aedes vexans, Anopheles quadrimaculatus, Culex pipiens,* and *Culex quinquefaxciatus.*

The term "tick" as used herein includes any type of tick, including but not limited to, deer ticks, the American dog tick (*Dermacentor variabilis*), *Ornithodoros parkeri, O. moubata,* and *Dermacentor andersoni.*

The term "cockroach" as used herein refers to any type of cockroach, including but not limited to the American cockroach (*Periplaneta americana*), German cockroach (*Blattella germanica*), oriental cockroach (*Blatta orientalis*), wood cockroach (*Parcoblatta pennsylvanica*), brownbanded cockroach (*Supella longipalpa*), and smokybrown cockroach (*Periplaneta fuliginosa*).

Other insect that can be treated by the repellant methods of the present invention include, but are not limited to: lice (Order Phthiraptera), such as head and body lice of humans, *Pediculus humanus capitis* and *P. H. humanus*; Fleas (Order Siphonaptera), such as cat and dog fleas, Ctenocephalides sp. human fleas, Echidnophaga, Pulex sp. Bees, wasps and ants (Order Hymenoptera) mites such as *Sarcoptes scabei* (human itch mite) the North American chigger or red bug, Trombicula sp. nematodes such as human parasitic nematodes, Silverfish (Order Thysanura), such as *Lepisma saccharina,* firebrat, *Thermobia domestica*; Termites (Order Isoptera) such as *Reticulitermes flavipes, Incisitermes minor, Marginitermes hubbardi,* and *Cryptotermes brevis*; Earwigs (Order Dermaptera); Psocids (Order Psocoptera) such as booklice; Beetles (Order Coleoptera), particularly wood eating beetles; Centipedes such as Lithobius, Geophilus, Scutigera and millipides such as *Julus terrestris*; Scorpions such as *Centruroides sculpturatus* and *Mastigoproctus gianteus*; etc.

Liquid repellant formulations may be aqueous-based or non-aqueous (i.e., organic solvents), or combinations thereof, and may be employed as foams, gels, suspensions, emulsions, microemulsions or emulsifiable concentrates or the like. The ingredients may include Theological agents, surfactants, emulsifiers, dispersants or polymers.

In one embodiment, a floor wax composition may include repellant compounds as described herein, in an amount effective to repel cockroaches that might otherwise feed upon the composition once applied to floors, or to simply repel cockroaches from floor surfaces to which they are applied.

As will be appreciated by a person skilled in the art, the repellant concentration will vary widely depending upon the nature of the particular formulation, particularly whether it is a concentrate or to be used directly. The repellant compound will be present in the composition in a concentration of at least about 0.0001% by weight and may be 10, 50, 99 or 100% by weight of the total composition. The repellant carrier may be from 0.1% to 99.9999% by weight of the total composition. The dry formulations will have from about 0.0001–95% by weight of the pesticide while the liquid formulations will generally have from about 0.0001–60% by weight of the solids in the liquid phase.

The formulations may be applied to the subject's skin, or may be applied to garments, belts, collars, or other articles worn by the subject from whom insects are to be repelled. The formulation may be applied to netting or screening that protects a subject, particularly a sleeping subject. The formulations may be applied to non-animal substrates from which insects are to be repelled, such as plants. Application to subjects or substrates may be carried out by spraying, dusting, sprinkling or the like.

The compounds according to the present invention may be employed alone or in mixtures with one another and/or with such solid and/or liquid dispersible carrier vehicles as described herein or as otherwise known in the art, and/or with other known compatible active agents, including, for example, insecticides, acaricides, rodenticides, fungicides, bactericides, nematocides, herbicides, fertilizers, growth-regulating agents, etc., if desired, in the form of particular dosage preparations for specific application made therefrom, such as solutions, emulsions, suspensions, powders, pastes, and granules as described herein or as otherwise known in the art which are thus ready for use.

The repellant compounds may be administered with other insect control chemicals, for example, the compositions of the invention may employ various chemicals that affect insect behavior, such as insecticides, attractants and/or repellents, or as otherwise known in the art. The repellant compounds may also be administered with chemosterilants.

The repellant compounds are suitably applied by any method known in the art including, for example, spraying, pouring, dipping, in the form of concentrated liquids, solutions, suspensions, sprays, powders, pellets, briquettes, bricks and the like, formulated to deliver a repellant effective concentration of the repellant compound. The repellant formulations may be applied in a repellant effective amount to an area of pest infestation or an area susceptible to infestation, a body of water or container, a barn, a carpet, pet bedding, an animal, clothing, skin, and the like.

The following examples are illustrative of the practice of the present invention and should not be construed as limiting. All percentages are by weight and all solvent mixture proportions are by volume unless otherwise noted.

EXAMPLE 1

Preparation of E-7-Phenylhept-4-enoic Acid

E-7-Phenylhept-4-enoic acid was prepared from commercially available dihydrocinnamaldehyde in five steps. Dihydrocinnamaldehyde was combined with the lithium salt of ethyl diethoxyphosphonioacetate in tetrahydrofuran at room temperature. The resulting unsaturated ester, ethyl 5-phenylpent-2-enoate, was purified by chromatography. The unsaturated ester was then reduced to the allylic alcohol, E-5-phenylpent-2-en-1-ol, by reaction with excess diisobutylaluminum hydride in tetrahydrofuran at −78° C. The purified alcohol was then converted to the bromide, E-1-bromo-5-phenylpent-2-ene, by reaction with triphenylphosphine and carbon tetrabromide in methylene chloride at 0° C. The purified bromide was then used to alkylate the sodium salt of diethyl malonate to provide the diester, methyl E-1-carbomethoxy-5-phenylhept-4-enoate. The diester was purified by chromatography and then subjected to saponification using methanolic sodium hydroxide. The diacid was purified by acid/base extraction and then used directly in the next step of the reaction sequence. Decarboxylation was effected by heating the neat diacid at 170° C. (under Ar) for 30 minutes. The product, E-7-phenylhept-4-enoic acid, was obtained in greater than 95% purity. Any residual diacid was removed by dissolving the acid in hexane and filtering. All compounds in the reaction sequence were fully characterized by spectral analysis (infrared and nuclear magnetic spectroscopy) and new compounds were analyzed by combustion analysis.

EXAMPLE 2

7-Phenylheptanoic Acid

7-Phenylheptanoic acid was prepared from E-7-phenylhept-4-enoic acid by hydrogenation at 40 psi using 5% palladium on carbon as the catalyst. Quantitative conversion of the alkene to the alkane was observed by thin layer chromatographic analysis. The product acid was purified by chromatography on silica gel and fully characterized by spectroscopic methods (infrared and nuclear magnetic resonance) and combustion analysis.

EXAMPLE 3

E-7-(4-Methoxyphenyl)hept-4-enoic Acid

E-7-(4-Methoxyphenyl)hept-4-enoic acid was prepared in the same fashion as E-7-phenylhept-4-enoic acid by substituting 3-(4-methoxyphenyl) propional for dihydrocinnamaldehyde as the starting material in the synthetic sequence. 3-(4-methoxyphenyl)propional was combined with the lithium salt of ethyl diethoxyphosphonioacetate in tetrahydrofuran at room temperature. The resulting unsaturated ester, ethyl 5-(4-methoxyphenyl)pent-2-enoate, was purified by chromatography. The unsaturated ester was then reduced with excess diisobutylaluminum hydride in tetrahydrofuran at −78° C. The purified alcohol was then converted to the bromide, E-1-bromo-5-(4-methoxyphenyl)pent-2-ene, by reaction with triphenylphosphine and carbon tetrabromide in methylene chloride at 0° C. The purified bromide was then used to alkylate the sodium salt of diethyl malonate to provide the diester, methyl E-1-carbomethoxy-5-(4-methoxyphenyl)hept-4-enoate. The diester was purified by chromatography and then subjected to saponification using methanolic sodium hydroxide. The diacid was purified by acid/base extraction and then used directly in the next step of the reaction sequence. Heating the neat diacid at 170° C. (under Ar) for 30 minutes effected decarboxylation. The product, E-7-(4-methoxyphenyl)hept-4-enoic acid, was obtained in greater than 95% purity. Any residual diacid was removed by dissolving the acid in hexane and filtering. All compounds in the reaction sequence were fully characterized by spectral analysis and new compounds were analyzed by combustion analysis.

EXAMPLE 4

E-7-(4-hydroxyphenyl)hept-4-enoic Acid

E-7-(4-hydroxyphenyl)hept-4-enoic acid was prepared from E-7-(4-methoxyphenyl)hept-4-enoic acid by removal of the methyl ether with boron tribromide. Boron tribromide was added to a solution of E-7-(4-methoxyphenyl)hept-4-enoic acid in methylene chloride at −78° C. and stirred for four hours. The product, E-7-(4-hydroxyphenyl)hept-4-enoic acid, was obtained by aqueous work-up of the reaction mixture followed by chromatography on silica gel, and was fully characterized by spectroscopic methods (infrared and nuclear magnetic resonance) and combustion analysis.

EXAMPLE 5

Ethyl E-7-(Cyclohexyl)hept-4-enoate (IBI218)

Ethyl E-7-(cyclohexyl)hept-4-enoate was prepared in two steps from the known compound 3-cyclohexylpropanal. A tetrahydrofuran solution of 3-cyclohexylpropanal was treated with vinyl magnesium bromide (as a solution in tetrahydrofuran) at 0° C. The resulting allyl alcohol derivative, 5-cyclohexyl-3-hydroxypent-1-ene, was purified by chromatography. The allylic alcohol was then dissolved in triethyl orthoacetate and heated to 140° C. to effect a Claisen rearrangement. The product, ethyl E-7-(cyclohexyl)hept-4-enoate, was obtained in >95% purity after chromatography. The product was fully characterized by spectral analysis(infrared and nuclear magnetic spectroscopy) and combustion analysis.

EXAMPLE 6

Ethyl E-7-((4-phenyl)phenyl)hept-4-enoate (IBI 221)

Ethyl E-7-((4-phenyl)phenyl)hept-4-enoate was prepared in two steps from the known compound 3-((4-phenyl)phenyl)-propanal. A tetrahydrofuran solution of 3-((4-phenyl)phenyl)propanal was treated with vinyl magnesium bromide (as a solution in tetrahydrofuran) at 0° C. The resulting allyl alcohol derivative, 5-((4-phenyl)phenyl)-3-hydroxypent-1-ene, was purified by chromatography. The allylic alcohol was then dissolved in triethyl orthoacetate and heated to 140 C. to effect a Claisen rearrangement. The product, ethyl E-7-((4-phenyl)phenyl)hept-4-enoate, was obtained in >95% purity after chromatography. The product was fully characterized by spectral analysis(infrared and nuclear magnetic spectroscopy) and combustion analysis.

EXAMPLE 7

E-7-(Cyclohexyl)hept-4-enoic Acid (IBI 172)

Ethyl E-7-(cyclohexyl)hept-4-enoate was saponified in methanolic sodium hydroxide at room temperature. The resulting acid,E-7-(cyclohexyl)hept-4-enoic acid, was obtained in >95% purity after chromatography. The product was fully characterized by spectral analysis (infrared and nuclear magnetic spectroscopy) and combustion analysis.

EXAMPLE 8

E-7-((4-phenyl)phenyl)hept-4-enoic Acid (IBI 165)

Ethyl E-7-((4-phenyl)phenyl)hept-4-enoate was saponified in methanolic sodium hydroxide at room temperature.

The resulting acid, E-7-((4-phenyl)phenyl)hept-4-enoic acid, was obtained in >95% purity after chromatography. The product was fully characterized by spectral analysis infrared and nuclear magnetic spectroscopy) and combustion analysis.

EXAMPLE 9

7-Phenyl-trans-(4,5-methano)heptanoic acid (IBI-215)

7-Phenyl-trans-(4,5-methano)heptanoic acid was prepared in one step from E-(7-phenyl)hept-4-enoic acid in high chemical yield. E-(7-phenyl)hept-4-enoic acid was added as a solution in dichloromethane to a preformed solution of Simmons-Smith reagent (generated by adding four equivalents of diiodomethane to two equivalents diethyl zinc in dichloromethane at 0° C.). The mixture was stirred for two hours at room temperature and then quenched at 0 C. by the addition of a saturated aqueous solution of ammonium chloride. The cyclopropane derivative, 7-phenyl-trans-(4,5-methano)heptanoic acid, was obtained in >95% purity after chromatography. The product was fully characterized by spectral analysis (nuclear magnetic spectroscopy) and combustion analysis.

EXAMPLE 10

7-Cyclohexyl-trans-(4,5-methano)heptanoic acid (IBI-216)

7-Cyclohexyl-trans-(4,5-methano)heptanoic acid was prepared in one step from E-(7-cyclohexyl)hept-4-enoic acid in high chemical yield. E-(7-cyclohexyl)hept-4-enoic acid was added as a solution in dichloromethane to a preformed solution of Simmons-Smith reagent (generated by adding four equivalents of diiodomethane to two equivalents diethyl zinc in dichloromethane at 0° C.). The mixture was stirred for two hours at room temperature and then quenched at 0° C. by the addition of a saturated aqueous solution of ammonium chloride. The cyclopropane derivative, 7-cyclohexyl-trans-(4,5-methano)heptanoic acid, was obtained in >95% purity after chromatography. The product was fully characterized by spectral analysis (nuclear magnetic spectroscopy) and combustion analysis.

EXAMPLE 11

7-(4-Phenyl)phenyl-trans-(4,5-methano)heptanoic acid, IBI-217

7-(4-Phenyl)phenyl-trans-(4,5-methano)heptanoic acid was prepared in one step from E-(4-phenyl)phenyl)hept-4-enoic acid in high chemical yield. E-(4-Phenyl)phenyl)hept-4-enoic acid was added as a solution in dichloromethane to a preformed solution of Simmons-Smith reagent (generated by adding four equivalents of diiodomethane to two equivalents diethyl zinc in dichloromethane at 0° C.). The mixture was stirred for two hours at room temperature and then quenched at 0 C. by the addition of a saturated aqueous solution of ammonium chloride. The cyclopropane derivative, 7-(4-phenyl)phenyl-trans-(4,5-methano) heptanoic acid, was obtained in >95% purity after chromatography. The product was fully characterized by spectral analysis (nuclear magnetic spectroscopy) and combustion analysis.

EXAMPLE 12

Bioassay of Compounds

Mosquito larval mortality was followed for three days in microtiter plates containing 160 $\mu$L sterile water, 1–4 $\mu$L of the test compound dissolved in dimethylsulfoxide, and 10 $\mu$L of 2% Brewer's yeast. Controls were run under the same conditions without the test compounds. Larval mortality in the controls was 3% for 1–3 $\mu$L dimethylsulfoxide, and up to 20% for 4 $\mu$L dimethylsulfoxide. Data for various compounds of the invention as an $LD_{50}$ are given in Table 1 below.

| Cmpd | Structure | $LC_{50}$ ± SEM | Formula | MW |
|---|---|---|---|---|
| IBI-215 | (phenyl-CH2-cyclopropane-CH2CH2-CO2H) | 0.18 ± 0.03 | $C_{14}H_{18}O_2$ | 218.29 |
| IBI-216 | (cyclohexyl-CH2-cyclopropane-CH2CH2-CO2H) | 0.3 ± 0.01 | $C_{14}H_{24}O_2$ | 224.34 |
| IBI-217 | (Ph-phenyl-CH2-cyclopropane-CH2CH2-CO2H) | 0.13 ± 0.04 | $C_{20}H_{22}O_2$ | 294.39 |

Ph means phenyl.

The examples and embodiments described herein are for illustrative purposes only and various modifications or changes in light thereof will be suggested to persons skilled in the art and are to be included within the spirit and purview of this application and the scope of the appended claims.

That which is claimed is:

1. A method for controlling an insect pest, comprising administering to said insect pest an insect pest-controlling effective amount of a compound selected from the group consisting of compounds of formula I, and salt, acid and ester forms thereof:

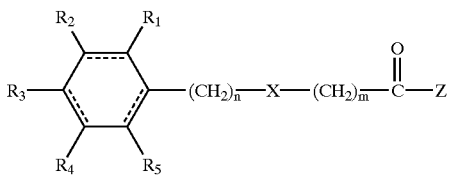

wherein:

X is cyclopropyl;

Z is selected from the group consisting of —OH, —NH$_2$, —NHR$_6$ and —OR$_6$ wherein R$_6$ is C1–C6 alkyl, alkenyl, optionally substituted cycloalkylalkyl, and optionally substituted aralkyl;

m ≧ 0 and n ≧ 1 and (m+n) can have any integer value from 1 to 12 inclusive; the ring bearing substituents R$_1$, R$_2$, R$_3$, R$_4$ and R$_5$ is a phenyl ring or a cyclohexyl ring, or a corresponding ring wherein one or more ring carbon atom(s) has been replaced by nitrogen atom(s);

R1, R2, R3, R4, and R5 are each independently selected from the group consisting of—H, —OH, halo, C1–C6 alkyl, C1–C6 alkoxy, nitro, amino, and phenyl; subject to the proviso that:

when the ring is a phenyl ring, a pair of R$_1$ and R$_2$, R$_2$ and R$_3$, or R$_3$ and R$_4$ on the phenyl ring may together represent —CR$_7$=CR$_8$-CR$_9$=CR$_{10}$-, to form with the phenyl ring illustrated above a naphthyl ring system, wherein R$_7$, R$_8$, R$_9$, and R$_{10}$ are each independently selected from the group consisting of —H, —OH, halo, nitro, amino, C$_1$–C$_6$ alkyl, and C1–C6 alkoxy.

2. A method according to claim 1, wherein said compound of Formula I has the formula

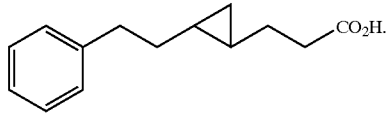

3. The method according to claim 1, wherein said compound of Formula I has the formula:

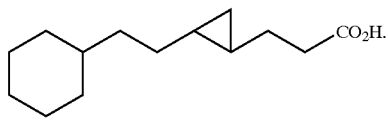

4. The method according to claim 1, wherein said compound of Formula I has the formula:

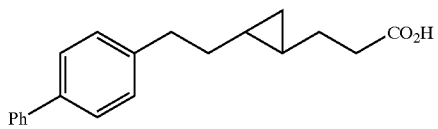

where Ph is phenyl.

5. A method according to claim 1, wherein R$_1$ is selected from the group consisting of hydroxy, bromo, fluoro, methyl, methoxy, propoxy, and ethoxy.

6. A method according to claim 1, wherein R$_1$ is selected from the group consisting of bromo and propoxy.

7. A method according to claim 1, wherein Z is OH.

8. A method according to claim 1, wherein Z is NH$_2$.

9. A method according to claim 1, wherein m is 2 to 12.

10. A method according to claim 1, wherein m is 3 to 10.

11. A method according to claim 1, wherein m is 4 to 8.

12. A method according to claim 1, wherein m is 4 to 6.

13. The method according to claim 1, wherein n is 2 to 12.

14. A method according to claim 1, wherein n is 3 to 10.

15. A method according to claim 1, wherein n is 4 to 8.

16. A method according to claim 1, wherein n is 4 to 6.

17. A method according to claim 1, wherein R$_2$ is H.

18. A method according to claim 1, wherein R$_3$ is H.

19. A method according to claim 1, wherein R$_5$ is H.

20. A method according to claim 1, wherein R$_2$ and R$_3$ are both H.

21. A method according to claim 1, wherein R$_2$ and R$_5$ are both H.

22. A method according to claim 1, wherein R$_3$ and R$_5$ are both H.

23. A method according to claim 1, wherein R$_2$, R$_3$ and R$_5$ are all H.

24. A method according to claim 1, wherein R$_1$ is a halogen.

25. A method according to claim 1, wherein R$_3$ is a halogen.

26. A method according to claim 1, wherein R$_1$ is an C1—C6 alkoxy.

27. A method according to claim 1, wherein R$_3$ is C1–C6 alkoxy.

28. A method according to claim 1, wherein R$_1$ and R$_3$ are both a halogen.

29. A method according to claim 1, wherein R$_1$ and R$_3$ are both an C1—C6 alkoxy.

30. A method according to claim 1, wherein said pest is an insect selected from the group consisting of coleopterans, lepidopterans, and dipterans.

31. A method according to claim 1, wherein said pest is a blood-sucking insect.

32. A method according to claim 1, wherein said pest is an insect of the suborder Nematocera.

33. A method according to claim 1, wherein said pest is an insect of the family Colicidae.

34. A method according to claim 1, wherein said pest is an insect of a subfamily selected from the group consisting of Culicinae, Corethrinae, Ceratopogonidae and Simuliidae.

35. A method according to claim 1, wherein said pest is an insect of a genus selected from the group consisting of Culex, Theobaldia, Aedes, Anopheles, Aedes, Forciponiyia, Culicoides and Helea.

36. A method according to claim 1, wherein said pest is an insect species selected from the group consisting of: Aedes aegypti, Culex quinquefasciatus, Anopheles albimanus, Anopheles quadrimaculatus, Lutzomyia ant hrophora, Culicoides variipennis, Stomoxys calcitrans, Musca domestica, Ctenocephalidesfeliz, and Heliothis virescens.

37. A method according to claim 1, wherein said pest is selected from the group consisting of flies, fleas, ticks, and lice.

38. A method according to claim 1, wherein said pest is a mosquito.

39. A method according to claim 1, wherein said pest is selected from the group consisting of beetles, caterpillars, and mites.

40. A method according to claim 1, wherein said pest is selected from the group consisting of ants and cockroaches.

41. A method of initiating a TMOF receptor-mediated biological response, comprising contacting to a TMOF receptor in vivo or in vitro for a time and in an amount sufficient to initiate a TMOF receptor-mediated biological response a compound selected from the group consisting of compounds of formula I, and salt, acid and ester forms thereof:

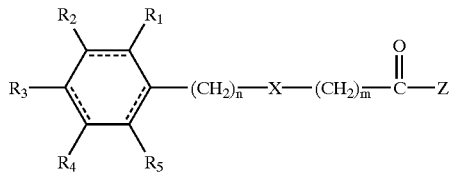

wherein:

X is cyclopropyl;

Z is selected from the group consisting of —OH, —NH$_2$, —NHR$_6$ and —OR$_6$ wherein R$_6$ is C1–C6 alkyl, alkenyl, optionally substituted cycloalkylalkyl, and optionally substituted aralkyl;

m$\geq$0 and n$\geq$1 and (m+n) can have any integer value from 1 to 12 inclusive; the ring bearing substituents R$_1$, R$_2$, R$_3$, R$_4$ and R$_5$ is a phenyl ring or a cyclohexyl ring, or a corresponding ring wherein one or more ring carbon atom(s) has been replaced by nitrogen atom(s);

R$_1$, R$_2$, R$_3$, R$_4$, and R$_5$ are each independently selected from the group consisting of—H, —OH, halo, C1–C6 alkyl, C1–C6 alkoxy, nitro, amino, and phenyl; subject to the proviso that:

when the ring is a phenyl ring, a pair of R$_1$ and R$_2$, R$_2$ and R$_3$, or R$_3$ and R$_4$ on the phenyl ring may together represent —CR7=CR8–CR9=CR10—, to form with the phenyl ring illustrated above a naphthyl ring system, wherein R$_7$, R$_8$, R$_9$, and R$_{10}$ are each independently selected from the group consisting of —H, —OH, halo, nitro, amino, C1–C6 alkyl, and C1–C6 alkoxy.

42. A method according to claim 41, wherein said compound of Formula I has the formula

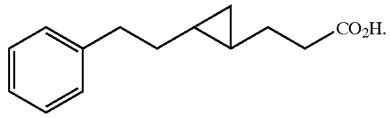

43. The method according to claim wherein said compound of Formula I has the formula:

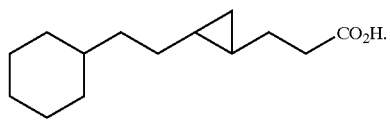

44. The method according to claim 41, wherein said compound of Formula I has the formula:

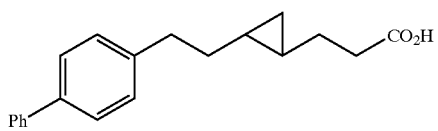

where Ph is phenyl.

45. A method according to claim 41, wherein said biological response is inhibition of biosynthesis of trypsin.

46. A method according to claim 41, wherein said contacting step is carried out in vivo in an insect pest.

47. A pest control composition comprising a pesticidal carrier and a pesticidal compound selected from the group consisting of compounds of formula I, and salt, acid and ester forms thereof:

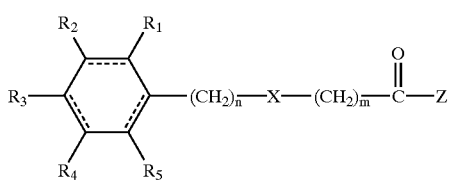

wherein:

X is cyclopropyl;

Z is selected from the group consisting of —OH, —NH$_2$, —NHR$_6$ and —OR$_6$ wherein R$_6$ is C1–C6 alkyl, alkenyl, optionally substituted cycloalkylalkyl, and optionally substituted aralkyl;

m$\geq$0 and n$\geq$1 and (m+n) can have any integer value from 1 to 12 inclusive; the ring bearing substituents R$_1$, R$_2$, R$_3$, R$_4$ and R$_5$ is a phenyl ring or a cyclohexyl ring, or a corresponding ring wherein one or more ring carbon atom(s) has been replaced by nitrogen atom(s);

R$_1$, R$_2$, R$_3$, R$_4$, and R$_5$ are each independently selected from the group consisting of —H, —OH, halo, C1–C6 alkyl, C1–C6 alkoxy, nitro, amino, and phenyl; subject to the proviso that:

when the ring is a phenyl ring, a pair of R$_1$ and R$_2$, R$_2$ and R$_3$, or R$_3$ and R$_4$ on the phenyl ring may together represent —CR$_7$=CR$_8$–CR$_9$=CR$_{10}$—, to form with the phenyl ring illustrated above a naphthyl ring system, wherein R$_7$, R$_8$, R$_9$, and R$_{10}$ are each independently selected from the group consisting of —H, —OH, halo, nitro, amino, C1–C6 alkyl and C1–C6 alkoxy.

48. A composition according to claim 47, herein said composition is a liquid composition, and wherein said liquid composition is selected from the group consisting of aqueous compositions nonaqueous compositions, and combinations thereof.

49. A composition according to claim 43, wherein said pesticidal carrier is included in said composition in an amount from 0.1% to 99.9999% by weight.

50. A composition according to claim 43, wherein said pesticidal carrier comprises an aqueous solution.

51. A composition according to 43, wherein said pesticidal carrier comprises an emulsion.

52. A composition according to claim 47, wherein said composition is a bait granule.

53. A composition according to claim 47, wherein said compound of Formula I has the formula

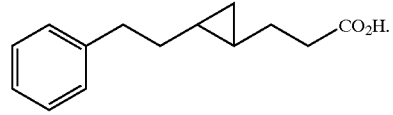

54. A composition according to claim 47, wherein said compound of Formula I has the formula:

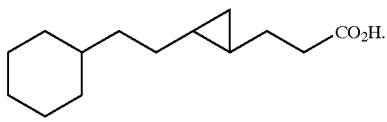

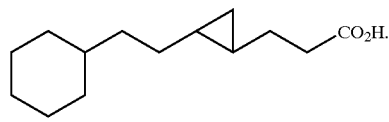

55. The composition according to claim 47, wherein said compound of Formula I has the formula:

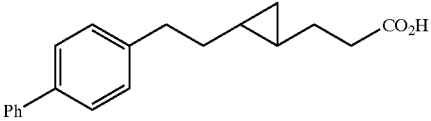

where Ph is phenyl.

56. A compound selected from the group consisting of compounds of formula I, and salt, acid and ester forms thereof:

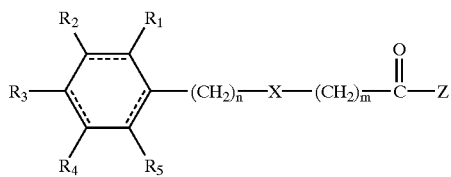

wherein:

X is cyclopropyl;

Z is selected from the group consisting of —OH, —NH$_2$, —NHR$_6$ and —OR$_6$ wherein R$_6$ is C1–C6 alkyl, alkenyl, optionally substituted cycloalkylalkyl, and optionally substituted aralkyl;

m≧0 and n≧1 and together total an integer from 1 to 12; the ring bearing substituents R$_1$, R$_2$, R$_3$, R$_4$ and R$_5$ is a phenyl ring or a cyclohexyl ring, or a corresponding ring wherein one or more ring carbon atom(s) has been replaced by nitrogen atom(s);

R$_1$, R$_2$, R$_3$, R$_4$, and R$_5$ are each independently selected from the group consisting of —H, —OH, halo, C1–C6 alkyl, C1–C6 alkoxy, nitro, amino, and phenyl; subject to the proviso that:

when the ring is a phenyl ring, a pair of R$_1$ and R$_2$, R$_2$ and R$_3$, or R$_3$ and R$_4$ on the phenyl ring may together represent —CR$_7$=CR$_8$-CR$_9$=CR$_{10}$—, to form with the phenyl ring illustrated above a naphthyl ring system, wherein R$_7$, R$_8$, R$_9$, and R$_{10}$ are each independently selected from the group consisting of —H, —OH, halo, nitro, amino, C1–C6 alkyl, and C1–C6 alkoxy.

57. The compound according to claim 56, wherein said compound of Formula I has the formula

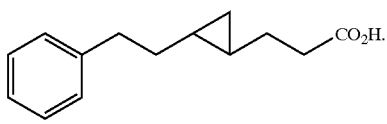

58. The compound according to claim 56, wherein said compound of Formula I has the formula:

59. The compound according to claim 56, wherein said compound of Formula I has the formula:

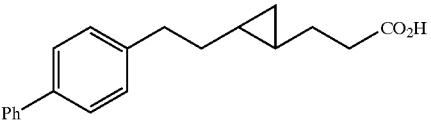

where Ph is phenyl.

60. The compound according to claim 56, wherein R$_1$ is selected from the group consisting of hydroxy, bromo, fluoro, methyl, methoxy, propoxy, and ethoxy.

61. The compound according to claim 56, wherein R$_1$ is selected from the group consisting of bromo and propoxy.

62. The compound according to claim 56, wherein Z is OH.

63. The compound according to claim 56, wherein Z is NH$_2$.

64. The compound according to claim 56, wherein m is 2 to 12.

65. The compound according to claim 56, wherein m is 3 to 10.

66. The compound according to claim 56, wherein m is 4 to 8.

67. The compound according to claim 56, wherein m is 4 to 6.

68. The compound according to claim 56, wherein n is 2 to 12.

69. The compound according to claim 56, wherein n is 3 to 10.

70. The compound according to claim 56, wherein n is 4 to 8.

71. The compound according to claim 56, wherein n is 4 to 6.

72. The compound according to claim 56, wherein R$_2$ is H.

73. The compound according to claim 56, wherein R$_3$ is H.

74. The compound according to claim 56, wherein R$_5$ is H.

75. The compound according to claim 56, wherein R$_2$ and R$_3$ are both H.

76. The compound according to claim 56, wherein R$_2$ and R$_5$ are both H.

77. The compound according to claim 56, wherein R$_3$ and R$_5$ are both H.

78. The compound according to claim 56, wherein R$_2$, R$_3$ and R$_5$ are all H.

79. The compound according to claim 56, wherein R$_1$ is a halogen.

80. The compound according to claim 56, wherein R$_3$ is a halogen.

81. The compound according to claim 56, to R$_1$ is C1–C6 alkoxy.

82. The compound according to claim 56, wherein R$_3$ is C1–C6 alkoxy.

83. The compound according to claim 56, wherein $R_1$ and $R_3$ are both halogen.

84. The compound according to claim 56, wherein R1 and R3 are both C1–C6 alkoxy.

85. A method according to claim 1, wherein the pest-controlling effective amount is a pesticidally effective amount of said compound.

86. A method according to claim 1, wherein the pest-controlling effective amount is a pest-repelling effective amount of said compound.

* * * * *